(12) United States Patent
Bathe et al.

(10) Patent No.: US 6,844,176 B1
(45) Date of Patent: Jan. 18, 2005

(54) **ALLELES OF THE LYSC GENE FROM *CORYNEBACTERIA***

(75) Inventors: Brigitte Bathe, Salzkotten (DE); Stephan Hans, Osnabrueck (DE)

(73) Assignee: Degussa AG, Duesseldorf (DE)

( * ) Notice: Subject to any disclaimer, the term of this patent is extended or adjusted under 35 U.S.C. 154(b) by 0 days.

(21) Appl. No.: 10/270,512

(22) Filed: Oct. 16, 2002

Related U.S. Application Data

(60) Provisional application No. 60/329,315, filed on Oct. 16, 2001.

(51) Int. Cl.$^7$ .................................................. C12N 9/10
(52) U.S. Cl. ..................... 435/193; 435/183; 435/252.3; 435/252.32; 435/320.1; 536/23.2
(58) Field of Search ................................ 435/183, 193, 435/252.3, 252.32, 320.1; 536/23.2

(56) References Cited

FOREIGN PATENT DOCUMENTS

JP    H6-261766    9/1994

OTHER PUBLICATIONS

Zhang et al. Accession Q9RQ25. May 1, 2000.*

* cited by examiner

*Primary Examiner*—Tekchand Saidha
*Assistant Examiner*—Christian L. Fronda
(74) *Attorney, Agent, or Firm*—Oblon, Spivak, McClelland, Maier & Neustadt, P.C.

(57) ABSTRACT

Alleles of the lysC gene from *corynebacteria* that code for desensitized aspartokinases, and to processes for the preparation of L-lysine using bacteria containing these alleles.

21 Claims, 1 Drawing Sheet

Figure 1: Map of plasmid pK18mobsacB_lysC_S301F
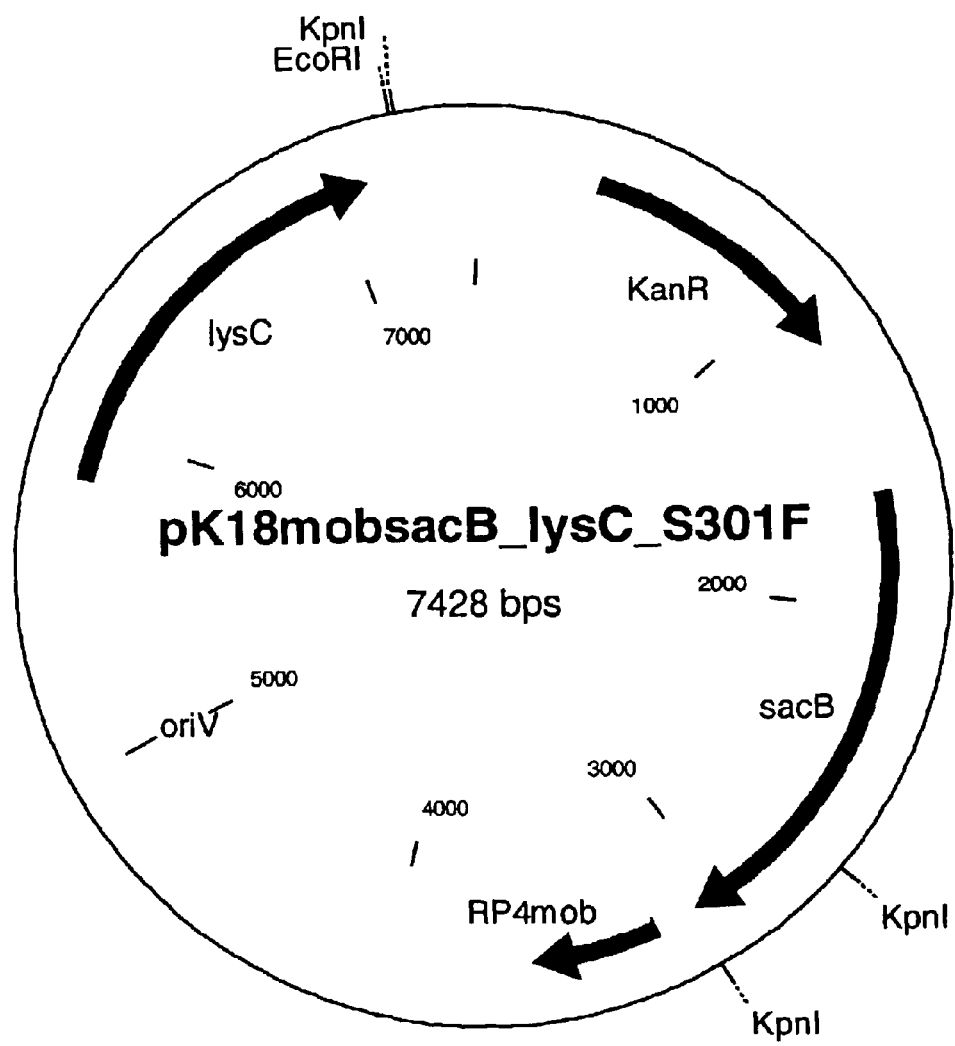

ALLELES OF THE LYSC GENE FROM CORYNEBACTERIA

CONTINUING APPLICATION DATA

This application claims priority to U.S. Provisional Application Ser. No. 60/329,315, filed on Oct. 16, 2001, the content of which are incorporated herein by reference.

BACKGROUND OF THE INVENTION

1. Field of the Invention

The present invention relates to alleles of the lysC gene from corynebacteria that code for desensitized aspartokinases, and processes for the preparation of L-lysine using bacteria containing these alleles.

2. Description of the Background

The amino acid L-lysine is used in human medicine and in the pharmaceutical industry, in the food industry and very particularly in animal nutrition.

It is known to prepare amino acids by the fermentation of strains of *corynebacteria*, especially *Corynebacterium glutamicum*. Because of their great importance, attempts are constantly being made to improve the preparative processes. Improvements to the processes may relate to measures involving the fermentation technology, for example stirring and oxygen supply, or the composition of the nutrient media, for example the sugar concentration during fermentation, or the work-up to the product form, for example by ion exchange chromatography, or the intrinsic productivity characteristics of the microorganism itself.

The productivity characteristics of these microorganisms are improved by using methods of mutagenesis, selection and mutant choice to give strains which are resistant to antimetabolites or auxotrophic for metaholites of regulatory significance, and produce amino acids. A known antimetabolite is the lysine analogue S-(2-aminoethyl)-L-cysteine (AEC).

An important reaction step in the biosynthesis of L-lysine is the aspartokinase reaction. The enzyme aspartokinase catalyzes the conversion of L-aspartic acid to aspartylphosphoric acid. The gene coding for aspartokinase is called lysC or ask. The nucleotide sequence of the lysC or ask gene from the wild-type strain *Corynebacterium glutamicum* ATCC 13032 is known and is described for example in Kalinowski et al. (Molecular Microbiology 5, 1197–204 (1991)) or Follettie (Journal of Bacteriology 175, 4096–4103 (1993)). The activity of the enzyme in the wild-type form is inhibited inter alia by mixtures of lysine and threonine, or mixtures of AEC and threonine, or lysine alone, or AEC alone.

The literature contains mutated forms of the lysC gene which were isolated after mutagenesis with e.g. N-methyl-N'-nitro-N-nitrosoguanidine and selection with the aid of AEC. These lysC alleles code for aspartokinases which, compared with the wild-type form, exhibit a lower sensitivity to inhibition by mixtures of lysine and threonine, or mixtures of AEC and threonine, or lysine alone, or AEC alone. In this connection the aspartokinases are said to be desensitized or feedback-resistant or AEC-resistant. L-lysine-producing strains typically contain such desensitized aspartokinases.

Examples of such desensitized aspartokinases from *corynebacteria* are described in EP-A-0387527, in U.S. Pat. No. 5,688,671 and in publicly accessible data banks for nucleotide sequences, for example that of the European Molecular Biologies Laboratories (EMBL, Heidelberg, Germany) or that of the National Center for Biotechnology Information (NCBI, Bethesda, Md., USA).

Methods of recombinant DNA technology have also been used for some years to improve L-amino acid-producing strains of *Corynebacterium* by amplifying individual amino acid biosynthesis genes and studying the effect on amino acid production.

SUMMARY OF THE INVENTION

The object which the inventors set out to achieve was to provide novel procedures for improving the preparation of L-lysine by fermentation.

The invention provides replicatable nucleotide sequences (DNA) originating from *corynebacteria*, especially *Corynebacterium glutamicum*, and coding for the enzyme aspartokinase, the corresponding amino acid sequences containing any proteogenic amino acid, except L.serine, in position 301 of SEQ ID No. 2.

Thus, the present invention includes a replicatable nucleic acid originating from *corynebacteria* and coding for an aspartokinase, wherein the amino acid sequence of the aspartokinase is SEQ ID NO: 2 in which the L-serine in position 301 is replaced by a different proteogenic amino acid.

The invention also provides a replicatable nucleotide sequence (DNA) originating from *corynebacteria*, especially *Corynebacterium glutamicum*, and coding for the enzyme aspartokinase, the corresponding amino acid sequence containing L-phenylalanine in position 301, as shown in SEQ ID No. 4.

The invention also provides a replicatable, preferably endogenous nucleotide sequence (DNA) originating from *corynebacteria*, especially *Corynebacterium glutamicum*, and coding for the enzyme aspartokinase, whose base sequence contains thymine in position 902, as shown in SEQ ID No. 3.

The present invention also provides a vector which contains the replicatable nucleic acid described above.

The present invention also provides a *Corynebacteria* transformed with the vector described above.

The present invention also provides a *Corynebacteria* which contain the nucleotide sequence described above.

The present invention also provides a process for the preparation of L-lysine or L-lysine-containing animal feed additives, comprising:

a) fermenting *corynebacteria* in which alleles of the endogenous lysC gene are overexpressed under conditions suitable for forming the lysC gene product aspartokinase; and b) isolating L-lysine or L-lysine-containing animal feed additive from the fermentation broth, wherein the *corynebacteria* produce L-lysine during the fermentation.

The present invention also provides a process for the preparation of L-lysine or L-lysine-containing animal feed additives, comprising:

a) fermenting *corynebacteria* containing an endogenous nucleotide sequences coding for the enzyme aspartokinase, the L-serine in position 301 of the corresponding amino acid sequences being replaced by another proteogenic amino acid, b) enriching the L-lysine in the fermentation broth, and c) isolating the L-lysine or L-lysine-containing animal feed additive from the fermentation broth, optionally with constituents of the fermentation broth and/or the biomass.

The present invention also provides a process for producing L-lysine, comprising fermenting the *Corynebacteria* described above in a fermentation broth under conditions that the *Corynebacteria* produce L-lysine, and isolating the L-lysine.

A more complete appreciation of the invention and many of the attendant advantages thereof will be readily obtained as the same becomes better understood by reference to the following Figures in conjunction with the detailed description below.

BRIEF DESCRIPTION OF THE FIGURES

FIG. 1: Map of plasmid pK18mobsaeB_lysC_S301F

The abbreviations and symbols used have the meanings given below. The numbers of base pairs indicated are approximate values obtained within the limits of reproducibility of the measurements.

KanR: kanamycin resistance gene
EcoRI: cleavage site of the restriction enzyme EcoRI
KpnI: cleavage site of the restriction enzyme KpnI
lysC: cloned DNA fragment containing the lysC_S301F allele
sacB: sacB gene
RP4-mob: mob region with the origin of replication for the transfer (oriT)
oriV: origin of replication V

DETAILED DESCRIPTION OF THE INVENTION

The term "L-lysine" or "lysine" mentioned hereafter is to be understood as meaning not only the bases but also the salts, e.g. lysine monohydrochloride or lysine sulfate.

The term "endogenous genes" or "endogenous nucleotide sequences" is to be understood as meaning the genes or nucleotide sequences present population of a species.

The invention also provides plasmids (vectors) which contain the nucleotide sequences according to the invention and optionally replicate in *corynebacteria*.

The invention also provides *corynebacteria* which contain the nucleotide sequences according to the invention and in which the nucleotide sequences coding for aspartokinase are preferably present in overexpressed form, a different proteogenic amino acid being contained in the corresponding amino acid sequences in position 301 of SEQ ID No. 2.

The term "overexpression" is to be understood as meaning an increase in the intracellular concentration or activity of the aspartokinases according to the invention.

Through the measures of overexpression, the activity or concentration of the appropriate protein is generally increased at least by 10%, 25%, 50%, 75%, 100%, 150%, 200%, 300%, 400% or 500%, and at most by up to 1000% or 2000%, based on the activity or concentration of the protein in the starting microorganism.

The invention provides a process for the preparation of L-lysine or L-lysine-containing animal feed additives, which comprises carrying out the following steps:

a) fermentation of *corynebacteria* containing endogenous nucleotide sequences coding for the enzyme aspartokinase, the L-serine in position 301 of the corresponding amino acid sequences being replaced by another proteogenic amino acid, preferably L-phenylalanine, b) enrichment of the L-lysine in the fermentation broth, and c) isolation of the L-lysine or L-lysine-containing animal feed additive from the fermentation broth, d) optionally with constituents of the fermentation broth and/or the biomass (>0 to 100%).

The term "proteogenic amino acids" is to be understood as meaning all amino acids which are constituents of proteins or polypeptides, and especially the following: L-aspartic acid, L-asparagine, L-threonine, L-serine, L-glutamic acid, L-glutamine, glycine, L-alanine, L-cysteine, L-valine, L-methionine, L-isoleucine, L-leucine, L-tyrosine, L-phenylalanine, L-histidine, L-lysine, L-tryptophan, L-proline and L-arginine.

The wild-type form of the lysC gene is contained in wild-type strains of *corynebacteria*, especially those of the genus *Corynebacterium*. It is shown in SEQ ID No. 1. The species *Corynebacterium glutamicum*, known to those skilled in the art, may be mentioned in particular in the case of the genus *Corynebacterium*. Examples of known wild-type strains of the species *Corynebacterium glutamicum* are:

*Corynebacterium glutamicum* ATCC13032
*Corynebacterium acetoglutamicum* ATCC15806
*Corynebacterium acetoacidophilum* ATCC13870
*Corynebacterium melassecola* ATCC17965
*Corynebacterium thermoaminogenes* FERM BP-1539
*Brevibacterium flavum* ATCC14067
*Brevibacterium lactofermentum* ATCC13869 and
*Brevibacterium divaricatum* ATCC14020.

Strains identified by "ATCC" can be obtained from the American Type Culture Collection (Manassas, Va., USA). Strains identified by "FERM" can be obtained from the National Institute of Advanced Industrial Science and Technology (AIST Tsukuba Central 6, 1-1-1 Higashi, Tsukuba Ibaraki, Japan). The listed strain of *Corynebacterium thermoaminogenes* (FERM BP-1539) and other strains (FERM BP-1540, FERM BP-1541 and FERM BP-1542) are described in U.S. Pat. No. 5,250,434, incorporated herein by reference; the deposits referenced above are also incorporated herein by reference.

Mutagenesis methods described in the prior art are used to produce the lysC alleles according to the invention which code for a feedback-resistant aspartokinase characterized by an amino acid replacement in position 301 of SEQ ID No. 2.

The mutagenesis can be effected using conventional in vivo mutagenesis processes employing mutagenic substances, for example N-methyl-N'-nitro-N-nitrosoguanidine, or ultraviolet light.

The mutagenesis can also be effected using in vitro methods such as treatment with hydroxylamine (Miller, J. H.: A Short Course in Bacterial Genetics. A Laboratory Manual and Handbook for *Escherichia coli* and Related Bacteria, Cold Spring Harbor Laboratory Press, Cold Spring Harbor, 1992; all incorporated herein by reference), or mutagenic oligonucleotides (T. A. Brown: Gentechnologie für Einsteiger, Spektrum Akademischer Verlag, Heidelberg, 1993, incorporated herein by reference), or the polymerase chain reaction (PCR), as described in the manual by Newton and Graham (PCR, Spektrum Akademischer Verlag, Heidelberg, 1994, incorporated herein by reference).

Further instructions on the production of mutations can be found in the prior art and in known textbooks on genetics and molecular biology, e.g. the textbook by Knippers ("Molekulare Genetik", 6th edition, Georg Thieme Verlag, Stuttgart, Germany, 1995, incorporated herein by reference), the textbook by Winnacker ("Gene und Klone", VCH Verlagsgesellschaft, Weinheim, Germany, 1990, incorporated herein by reference) or the textbook by Hagemann ("Allgemeine Genetik", Gustav Fischer Verlag, Stuttgart, 1986, incorporated herein by reference).

When using in vivo mutagenesis processes, the mutagenized population of the bacterial strain is applied to an AEC-containing minimum agar and the culture is incubated at a temperature of approx. 25 to 35° C. Of the AEC-resistant mutants, those which produce L-lysine are then chosen. The lysC alleles contained in the mutants can then be isolated, examined and sequenced. Relevant instructions can be found for example in Kalinowski et al. (Molecular and General Genetics 224, 317–324 (1990), incorporated herein by reference), Kalinowski et al. (Molecular Microbiology 5, 1197–204 (1991), incorporated herein by reference) or Follettie et al. (Journal of Bacteriology 175, 4096–4103 (1993), incorporated herein by reference). Sequencing instructions can be found for example in Sanger et al. (Proceedings of the National Academy of Sciences of the United States of America 74, 5463–5467 (1977), incorporated herein by reference).

When using in vitro methods, the lysC gene described in the prior art is amplified with the aid of the polymerase chain reaction starting from isolated total DNA of a wild-type strain, and optionally cloned into suitable plasmid vectors, and the DNA is then subjected to the mutagenesis process. Those skilled in the art can find instructions on the amplification of DNA sequences with the aid of the polymerase chain reaction (PCR) in the manual by Gait: Oligonucleotide Synthesis: A Practical Approach (IRL Press, Oxford, UK, 1984, incorporated herein by reference) and in Newton and Graham: PCR (Spektrum Akademischer Verlag, Heidelberg, Germany, 1994, incorporated herein by reference), inter alia. Suitable lysC alleles are then selected by the processes described above and examined.

The work on the present invention made it possible to isolate the novel lysC allele, shown in SEQ ID No. 3, coding for a feedback-resistant aspartokinase.

In general, the first coding codon, namely the GTG codon, of the coding region of the lysC gene, shown in SEQ ID No. 1, or of the coding region of the lysC allele, shown in SEQ ID No. 3, is translated in the host as L-methionine or formylmethionine.

It is also known that enzymes inherent in the host, or so-called aminopeptidases, are capable of cleaving the N-terminal amino acid, L-methionine, of the protein formed.

The lysC alleles according to the invention can be transferred to suitable strains by the gene replacement method as described in Schwarzer and Pühler (Bio/Technology 9, 84–87 (1991), incorporated herein by reference) or Peters-Wendisch et al. (Microbiology 144, 915–927 (1998), incorporated herein by reference). To do this, the appropriate lysC allele is cloned into a vector that is not replicative for C. glutamicum, for example pK18mobsacB or pK19mobsacB (Jäger et al., Journal of Bacteriology 174, 5462–65 (1992), incorporated herein by reference) or pCR®Blunt (Invitrogen, Groningen, The Netherlands; Bernard et al., Journal of Molecular Biology 234, 534–541 (1993), incorporated herein by reference), and said vector is then transferred to the desired C. glutamicum host by transformation or conjugation. The mutation is successfully incorporated by homologous recombination by means of a first crossover event to effect integration and by means of a suitable second crossover event to effect excision in the target gene or in the target sequence.

The work on the present invention further revealed that the production of L-lysine improves after overexpression of the lysC alleles according to the invention.

Overexpression can be achieved by increasing the copy number of the appropriate genes or mutating the promoter and regulatory region or the ribosome binding site located upstream from the structural gene. Expression cassettes incorporated upstream from the structural gene work in the same way. Inducible promoters additionally make it possible to increase expression in the course of L-lysine production by fermentation. Measures for prolonging the life of the mRNA also improve expression. Furthermore, the enzyme activity is also enhanced by preventing the degradation of the enzyme protein. The genes or gene constructs can either be located in plasmids of variable copy number or be integrated and amplified in the chromosome. Alternatively, it is also possible to achieve overexpression of the genes in question by changing the composition of the media and the culture technique.

Plasmids which are replicated in corynebacteria are suitable for increasing the copy number of the lysC alleles according to the invention. Numerous known plasmid vectors, e.g. pZ1 (Menkel et al., Applied and Environmental Microbiology (1989) 64, 549–554, incorporated herein by reference), pEKEx 1 (Eikmanns et al., Gene 102, 93–98 (1991), incorporated herein by reference) or pHS2-1 (Sonnen et al., Gene 107, 69–74 (1991), incorporated herein by reference), are based on the cryptic plasmid pHM1519, pBL1 or pGA1. Other plasmid vectors, e.g. those based on pCG4 (U.S. Pat. No. 4,489,160, incorporated herein by reference), pNG2 (Serwold-Davis et al., FEMS Microbiology Letters 66, 119–124 (1990), incorporated herein by reference) or pAG1 (U.S. Pat. No. 5,158,891, incorporated herein by reference), can be used in the same way.

Another possible method of increasing the copy number is that of chromosomal gene amplification as described for example by Reinscheid et al. (Applied and Environmental Microbiology 60, 126–132 (1994), incorporated herein by reference) for the duplication or amplification of the hom-thrB operon. In this method the complete gene or allele is cloned into a plasmid vector capable of replicating in a host (typically E. coli), but not in C. glutamicum. Examples of suitable vectors are pSUP301 (Simon et al., Bio/Technology 1, 784–791 (1983), incorporated herein by reference), pK18mob or pK19mob (Schäfer et al., Gene 145, 69–73 (1994), incorporated herein by reference), pGEM-T (Promega Corporation, Madison, Wis., USA), pCR2.1-TOPO (Shuman, Journal of Biological Chemistry 269, 32678–84 (1994), incorporated herein by reference; U.S. Pat. No. 5,487,993, incorporated herein by reference), pCR®Blunt (Invitrogen, Groningen, The Netherlands; Bernard et al., Journal of Molecular Biology 234, 534–541 (1993), incorporated herein by reference), pEM1 (Schrumpf et al., Journal of Bacteriology 173, 4510–4516 (1991), incorporated herein by reference) or pBGS8 (Spratt et al., Gene 41, 337–342 (1986), incorporated herein by reference). The plasmid vector containing the gene or allele to be amplified is then transferred to the desired strain of C. glutamicum by conjugation or transformation. The method of conjugation is described for example in Schäfer et al. (Applied and Environmental Microbiology 60, 756–759 (1994), incorporated herein by reference). Methods of transformation are described for example in Thierbach et al. (Applied Microbiology and Biotechnology 29, 356–362 (1988), incorporated herein by reference), Dunican and Shivnan (Bio/Technology 7, 1067–1070 (1989), incorporated herein by reference) and Tauch et al. (FEMS Microbiological Letters 123, 343–347 (1994), incorporated herein by reference). After homologous recombination by means of a crossover event, the resulting strain contains at least two copies of the gene or allele in question.

In addition, for the production of L-amino acids, it can be advantageous not only to use the lysC alleles according to the invention, but also simultaneously to enhance or, in particular, overexpress one or more enzymes of the particular biosynthetic pathway, glycolytic enzymes, enzymes of the anaplerotic metabolism, enzymes of the citric acid cycle, enzymes of the pentose phosphate cycle, enzymes of amino acid export and optionally regulatory proteins. The use of endogenous genes is generally preferred.

The term "endogenous genes" or "endogenous nucleotide sequences" is to be understood as meaning the genes or nucleotide sequences, and their alleles, present in the population of a species.

Thus, for the preparation of L-lysine, it is possible not only to use the variant of the lysC gene, but also simultaneously to enhance or, in particular, overexpress one or more endogenous genes selected from the group comprising:

the dapA gene coding for dihydrodipicolinate synthase (EP-B 0 197 335, incorporated herein by reference), the gap gene coding for glyceraldehyde-3-phosphate dehydrogenase (Eikmanns (1992), Journal of Bacteriology 174, 6076–6086, incorporated herein by reference), the eno gene coding for enolase (DE 19947791.4, incorporated herein by reference), the tpi gene coding for triose phosphate isomerase (Eikmanns (1992), Journal of Bacteriology 174, 6076–6086, incorporated herein by reference), the pgk gene coding for 3-phosphoglycerate kinase (Eikmanns (1992), Journal of Bacteriology 174, 6076–6086, incorporated herein by reference), the zwf gene coding for glucose-6-phosphate dehydrogenase (JP-A-09224661; EP-A-1108790, incorporated herein by reference), the pyc gene coding for pyruvate carboxylase (DE-A-198 31 609, incorporated herein by reference; EP-A-1108790, incorporated herein by reference), the mqo gene coding for malate quinone oxidoreductase (Molenaar et al., European Journal of Biochemistry 254, 395–403 (1998), incorporated herein by reference), the lysC gene coding for a feedback-resistant aspartate kinase (Accession No. P26512, incorporated herein by reference; EP-B-0387527, incorporated herein by reference; EP-A-0699759, incorporated herein by reference; WO 00/63388, incorporated herein by reference), the lysE gene coding for the lysine export protein (DE-A-195 48 222, incorporated herein by reference), the zwa1 gene coding for the Zwa1 protein (DE:19959328.0, incorporated herein by reference, DSM 13115, incorporated herein by reference), the gnd gene coding for 6-phosphogluconate dehydrogenase (WO 01/71012, incorporated herein by reference) and the opcA gene coding for a subunit of glucose-6-phosphate dehydrogenase (sequence no. 79 from WO 01/00844, incorporated herein by reference; WO 01/04322, incorporated herein by reference).

6-Phosphogluconate dehydrogenase can also be enhanced inter alia by amino acid replacements, for example by replacing L-proline with L-serine, L-leucine, L-isoleucine or L-threonine in position 158 of the enzyme protein, and/or by replacing L-serine with L-phenylalanine or L-tyrosine in position 361 of the enzyme protein.

The glucose-6-phosphate dehydrogenase subunit can also be enhanced inter alia by amino acid replacements, for example by replacing L-serine with L-phenylalanine or L-tyrosine in position 312 of the enzyme protein.

Furthermore, for the production of L-lysine, it can be advantageous not only to use the variant of the lysC gene, but also simultaneously to attenuate or, in particular, decrease the expression of, one or more endogenous genes selected from the group comprising;

the pck gene coding for phosphoenolpyruvate carboxykinase (DE 199 50 409.1, incorporated herein by reference, DSM 13047, incorporated herein by reference), the pgi gene coding for glucose-6-phosphate isomerase (US 09/396,478, incorporated herein by reference, DSM 12969, incorporated herein by reference), the poxB gene coding for pyruvate oxidase (DE 19951975.7, incorporated herein by reference, DSM 13114, incorporated herein by reference), the zwa2 gene coding for the Zwa2 protein (DE 19959327.2, incorporated herein by reference, DSM 13113, incorporated herein by reference), the fda gene coding for fructose-1,6-bisphosphate aldolase (Accession No. X17313, incorporated herein by reference; von der Osten et al., Molecular Microbiology 3 (11), 1625–1637 (1989), incorporated herein by reference), the hom gene coding for homoserine dehydrogenase (EP-A-0131171, incorporated herein by reference), the leuB gene coding for isopropyl malate dehydrogenase (Pátek et al., Applied Environmental Microbiology 50, 43–47 (1989) incorporated herein by reference, Accession No. Y09578, incorporated herein by reference), the leuC gene coding for isopropyl malate dehydratase (Accession No. AX121536, sequence no. 1452 from patent EP 1108790, all incorporated herein by reference, Accession No. AX063983. incorporated herein by reference, sequence no. 265 from patent WO 01/00843, incorporated herein by reference), the thrB gene coding for homoserine kinase (Peoples, O. W. et al., Molecular Microbiology 2, 63–72 (1988), incorporated herein by reference) and the pfkB gene coding for phosphofructokinase (SEQ ID No. 57 from WO 01/00844, incorporated herein by reference).

In this context the term "attenuation" describes the decrease or switching-off, in a microorganism, of the intracellular activity of one or more enzymes/proteins coded for by the appropriate DNA, for example by using a weak promoter, or using a gene or allele which codes for an appropriate enzyme with a low activity, or inactivating the appropriate gene or enzyme/protein, and optionally combining these measures.

The attenuation measures generally reduce the activity or concentration of the appropriate protein to 0 to 75%, 0 to 50%, 0 to 25%, 0 to 10% or 0 to 5% of the activity or concentration of the wild-type protein or of the activity or concentration of the protein in the starting microorganism.

Isopropyl malate dehydrogenase can also be attenuated inter alia by means of amino acid replacements, for example by replacing L-glycine with L-aspartate, L-asparagine or L-glutamate in position 131 of the enzyme protein.

Isopropyl malate dehydratase can also be attenuated inter alia by means of amino acid replacements, for example by replacing L-arginine with L-serine in position 451 or by replacing L-glycine with L-aspartate in position 456 of the enzyme protein, or a combination thereof.

Homoserine dehydrogenase can also be attenuated inter alia by means of amino acid replacements, for example by replacing L-asparagine with L-threonine or L-serine in position 118 or by replacing L-leucine with L-proline in position 160 of the enzyme protein, or a combination thereof.

Phosphofructokinase can also be attenuated inter alia by means of amino acid replacements, for example by replacing L-leucine with L-alanine, L-glycine or L-proline in position 109 of the enzyme protein.

The microorganisms prepared according to the invention are also provided by the invention and can be cultivated continuously or discontinuously by the batch process, the fed batch process or the repeated fed batch process for the purpose of L-amino acid production. A summary of known cultivation methods is described in the textbook by Chmiel (Bioprozesstechnik 1. Einführung in die Bioverfahrenstechnik (Gustav Fischer Verlag, Stuttgart, 1991), incorporated herein by reference) or in the textbook by Storhas (Bioreaktoren und periphere Einrichtungen (Vieweg Verlag, Brunswick/Wiesbaden, 1994), incorporated herein by reference).

The culture medium to be used must appropriately meet the demands of the strains. Descriptions of culture media for various microorganisms can be found in "Manual of Methods for General Bacteriology" of the American Society for Bacteriology (Washington D.C., USA, 1981), incorporated herein by reference.

Carbon sources which can be used are sugars and carbohydrates, e.g. glucose, sucrose, lactose, fructose, maltose, molasses, starch and cellulose, oils and fats, for example soya bean oil, sunflower oil, groundnut oil and coconut fat, fatty acids, for example palmitic acid, stearic acid and linoleic acid, alcohols, for example glycerol and ethanol, and organic acids, for example acetic acid. These substances can be used individually or as a mixture.

Nitrogen sources which can be used are organic nitrogen-containing compounds such as peptones, yeast extract, meat extract, malt extract, corn steep liquor, soya bean flour and urea, or inorganic compounds such as ammonium sulfate, ammonium chloride, ammonium phosphate, ammonium carbonate and ammonium nitrate. The nitrogen sources can be used individually or as a mixture.

Phosphorus sources which can be used are phosphoric acid, potassium dihydrogenphosphate or dipotassium hydrogenphosphate or the corresponding sodium salts. The culture medium must also contain metal salts, for example magnesium sulfate or iron sulfate, which are necessary for growth. Finally, essential growth-promoting substances such as amino acids and vitamins can be used in addition to the substances mentioned above. Suitable precursors can also be added to the culture medium. Said feed materials can be added to the culture all at once or fed in appropriately during cultivation.

The pH of the culture is controlled by the appropriate use of basic compounds such as sodium hydroxide, potassium hydroxide, ammonia or aqueous ammonia, or acidic compounds such as phosphoric acid or sulfuric acid. Foaming can be controlled using antifoams such as fatty acid polyglycol esters. The stability of plasmids can be maintained by adding suitable selectively acting substances, for example antibiotics, to the medium. Aerobic conditions are maintained by introducing oxygen or oxygen-containing gaseous mixtures, for example air, into the culture. The temperature of the culture is normally 20° C. to 45° C. and preferably 25° C. to 40° C. Culture is continued until the formation of the desired product has reached a maximum. This objective is normally achieved within 10 hours to 160 hours.

Methods of determining L-amino acids are known from the prior art. For example, they can be analyzed by anion exchange chromatography followed by ninhydrin derivation, as described in Spackman et al. (Analytical Chemistry 30, 1190 (1958), incorporated herein by reference), or by reversed phase HPLC, as described in Lindroth et al. (Analytical Chemistry 51, 1167–1174 (1979), incorporated herein by reference).

The process according to the invention is used to prepare L-lysine.

The concentration of L-lysine can optionally be adjusted to the desired value by adding L-lysine.

EXAMPLES

Having generally described this invention, a further understanding can be obtained by reference to certain specific examples which are provided herein for purposes of illustration only and are not intended to be limiting unless otherwise specified.

Example 1

Amplification and Sequencing of the DNA of the lysC Allele from the Strain DM689

The *Corynebacterium glutamicum* strain DM689 was prepared from *C. glutamicum* ATCC13032 by multiple non-directed mutagenesis, selection and mutant choice. The strain is resistant to the lysine analogue S-(2-aminoethyl)-L-cysteine and the threonine analogue DL-hydroxynorvaline.

Chromosomal DNA is isolated from the strain DM689 by the conventional methods (Eikmanns et al., Microbiology 140, 1817–1828 (1994), incorporated herein by reference). The polymerase chain reaction is used to amplify a DNA segment carrying the lysC gene or allele. The following oligonucleotide primers are chosen for the PCR on the basis of the sequence of the lysC gene which is known for *C. glutamicum* (Kalinowski et al., Molecular Microbiology 5 (5), 1197–1204 (1991), incorporated herein by reference; Accession Number X57226, incorporated herein by reference):

lysCmfeA (SEQ ID No. 6):
5' ta caa ttg-tcc ggt gtc tga cca cgg tg 3'
lysCecoE (SEQ ID No. 7):
5' ac gaa ttc-gct ggg aaa ttg cgc tct tcc 3'

The primers shown are synthesized by MWG Biotech (Ebersberg, Germany) and the PCR is carried out by the standard method of Innis et al. (PCR protocols. A Guide to Methods and Applications, 1990, Academic Press, incorporated herein by reference). The primers enable the amplification of an approx. 1.70 kb DNA segment carrying the lysC allele (SEQ ID No. 5). The primers also contain the sequences for cleavage sites of the restriction endonucleases MfeI and EcoRI, which are underlined in the nucleotide sequence shown above.

The amplified DNA fragment of approx. 1.70 kb, carrying the lysC allele of the strain DM689, is identified by electrophoresis in 0.8% agarose gel, isolated from the gel and purified by the conventional methods (QIAquick Gel Extraction Kit, Qiagen, Hilden).

The nucleotide sequence of the amplified DNA fragment or PCR product is determined by MWG Biotech (Ebersberg, Germany) by sequencing. The sequence of the PCR product is shown in SEQ ID No. 5. The sequence of the coding region is reproduced in SEQ ID No. 3. The amino acid sequence of the corresponding aspartate kinase protein, found with the help of the Patentin program, are shown in SEQ ID No. 4.

Located in position 902 of the nucleotide sequence of the coding region of the lysC allele from the strain DM689, i.e. in position 1230 of the nucleotide sequence shown in SEQ ID No. 5, is the base thymine. Located in the corresponding position of the wild-type gene is the base cytosine (SEQ ID No. 1).

Located in position 301 of the amino acid sequence of the aspartate kinase from the strain DM689 is the amino acid phenylalanine (SEQ ID No. 4). Located in the corresponding position of the wild-type protein is the amino acid serine (SEQ ID No. 2).

The lysC allele, which contains the base thymine in position 902 of the coding region and accordingly codes for an aspartate kinase containing the amino acid phenylalanine in position 301 of the amino acid sequence, is called the lysC_S301F allele hereafter. In the name "lysC_S301F", S represents L-serine, F represents L-phenylalanine and 301 indicates the position of the amino acid replacement (cf. SEQ ID No. 2 and 4).

Example 2

Replacement of the lysC Wild-type Gene from the Strain DM1637 with the lysC_S301F Allele The *Corynebacterium glutamicum* strain DM1637 was prepared from *C. glutamicum* ATCC21527 by multiple non-directed mutagenesis, selection and mutant choice. The strain is resistant to the lysine analogue S-(2-aminoethyl)-L-cysteine and auxotrophic for the amino acids L-methionine and L-threonine.

2.1 Preparation of a DNA Fragment Containing the Region of the lysC_S301F Allele in which the S301F Mutation Is Located The approx. 1.70 kb DNA fragment described in Example 1, containing the is lysC_S301F allele (SEQ ID No. 5), is cleaved with the restriction endonucleases MfeI and EcoRI, identified by electrophoresis in 0.8% agarose gel and then isolated from the gel and purified by the conventional methods (QIAquick Gel Extraction Kit, Qiagen, Hilden).

2.2 Construction of the Replacement Vector pK18mobsacB_lysC_S301F

The approx. 1.70 kb DNA fragment described in Example 2.1, cleaved with the restriction endonucleases MfeI and EcoRI and containing the lysC_S301F allele, is incorporated into the chromosome of the *C. glutamicum* strain DM1637 by means of replacement mutagenesis with the aid of the sacB system described in Schäfer et al. (Gene 14, 69–73 (1994), incorporated herein by reference). This system makes it possible to prepare or select allele replacements that take place through homologous recombination.

The mobilizable cloning vector pK18mobsacB is digested with the restriction enzyme EcoRI and the ends are dephosphorylated with alkaline phosphatase (Boehringer Mannheim, Germany). The vector prepared in this way is mixed with the approx. 1.70 kb lysC_S301F fragment digested with the restriction enzymes MfeI and EcoRI, and the mixture is treated with T4 DNA ligase (Amersham-Pharmacia, Freiburg, Germany).

The *E. coli* strain S17-1 (Simon et al., Bio/Technologie 1, 784–791, 1993) is then transformed with the ligation mixture (Hanahan, in: DNA Cloning. A Practical Approach. Vol. 1, ILR-Press, Cold Spring Harbor, N.Y., 1989, incorporated herein by reference). The plasmid-carrying cells are selected by plating the transformation mixture on LB agar (Sambrook et al., Molecular Cloning: A Laboratory Manual. 2nd edition. Cold Spring Harbor, N.Y., 1989, incorporated herein by reference) supplemented with 25 mg/l of kanamycin.

Plasmid DNA is isolated from a transformant with the aid of the QIAprep Spin Miniprep Kit from Qiagen and checked by restriction cleavage with the enzyme KpnI followed by agarose gel electrophoresis. The plasmid is called pK18mobsacB_lysC_S301F and is shown in FIG. 1.

2.3 Allele Replacement

Vector pK18mobsacB_lysC_S301F mentioned in Example 2.2 is transferred to the *C. glutamicum* strain DM1637 by conjugation using a protocol of Schäfer et al. (Journal of Microbiology 172, 1663–1666 (1990), incorporated herein by reference). The vector cannot replicate independently in DM1637 and is only retained in the cell when it is integrated in the chromosome as the result of a recombination event. Transconjugants, i.e. clones with integrated pK18mobsacB_lysC_S301F, are selected by plating the conjugation mixture on LB agar (Sambrook et al., Molecular Cloning: A Laboratory Manual. 2nd edition. Cold Spring Harbor, N,Y., 1989, incorporated herein by reference) supplemented with 15 mg/l of kanamycin and 50 mg/l of nalidixic acid. Kanamycin-resistant transconjugants are streaked on plates of LB agar supplemented with 25 mg/l of kanamycin, and incubated for 24 hours at 33° C. To select mutants in which excision of the plasmid has taken place as the result of a second recombination event, the clones are cultivated non-selectively in LB liquid medium for 30 hours and then streaked on LB agar supplemented with 10% of sucrose, and incubated for 24 hours.

Like the starting plasmid pK18mobsacB, plasmid pK18mobsacB_lysC_S301F contains not only the kanamycin resistance gene but also a copy of the sacB gene coding for the levan sucrase from *Bacillus subtilis*. Expression inducible by sucrose leads to the formation of levan sucrase, which catalyzes the synthesis of the product levan, toxic to *C. glutamicum*. Therefore, the only clones that grow on LB agar supplemented with sucrose are those in which the integrated pK18mobsacB_lysC_S301F has excised as the result of a second recombination event. Depending on the location of the second recombination event in relation to the mutation site, allele replacement or incorporation of the mutation takes place in the excision or the original copy remains in the chromosome of the host.

20 clones with the phenotype "growth in the presence of sucrose" and "non-growth in the presence of kanamycin" are examined using the LightCycler from Roche Diagnostics (Mannheim, Germany) in order to detect whether the lysC_S301F allele or the original wild-type lysC allele is present. The LightCycler instrument is a combination of a thermal cycler and a fluorimeter.

In the first phase an approx. 300 bp DNA segment containing the mutation site is amplified by the PCR (Innis et al., PCR Protocols. A Guide to Methods and Applications, 1990, Academic Press, incorporated herein by reference) using the following oligonucleotide primers:
LC-lysC1-fbr (SEQ ID No. 8):
5' aaccgttctgggtatttccg 3'
LC-lysC2-fbr (SEQ ID No. 9):
5' tccatgaactctgcggtaac 3'

In the second phase, with two additional oligonucleotides of different lengths and labelled with different fluorescent dyes (LightCycler(LC)-Red640 and fluorescein), which hybridize in the region of the mutation site, and using the Fluorescence Resonance Energy Transfer (FRET) method, the presence of the mutation is detected by melting curve analysis (Lay et al., Clinical Chemistry, 43, 2262–2267 (1997), incorporated herein by reference).

lys301FC (SEQ ID No. 10):
5' LC-Red640-tctacagaaaagacgttctg-(P) 3'
lys301FA (SEQ ID No. 11):
5'acgagggcaggtgaaggtgatgtcggtggtgccgt-fluorescein 3'

The illustrated primers for the PCR are synthesized by MWG Biotech and the illustrated oligonucleotides for the hybridization are synthesized by TIB MOLBIOL (Berlin, Germany).

A clone containing the base thymine in position 902 of the coding region, and hence possessing the lysC_S301F allele, was identified in this way.

The strain was called *C. glutamicum* DM1637_lysC_S301F.

Example 3

Preparation of Lysine

The *C. glutamicum* strain DM1637_lysC_S301F obtained in Example 2 is cultivated in a nutrient medium suitable for the production of lysine, and the lysine content is determined in the culture supernatant.

To do this, the strain is first incubated on an agar plate for 24 hours at 33° C. This agar plate culture is used to inoculate a preculture (10 ml of medium in a 100 ml conical flask). MM medium is used as the medium for the preculture. The preculture is incubated on a shaker at 240 rpm for 24 hours at 33° C. This preculture is used to inoculate a main culture so that the initial OD (660 nm) of the main culture is 0.1. MM medium is also used for the main culture.

| MM medium | |
|---|---|
| CSL | 5 g/l |
| MOPS | 20 g/l |
| Glucose (separately autoclaved) | 50 g/l |
| Salts: | |
| $(NH_4)_2SO_4$ | 25 g/l |
| $KH_2PO_4$ | 0.1 g/l |
| $MgSO_4.7H_2O$ | 1.0 g/l |
| $CaCl_2.2H_2O$ | 10 mg/l |
| $FeSO_4.7H_2O$ | 10 mg/l |
| $MnSO_4.H_2O$ | 5.0 mg/l |
| Biotin (sterile-filtered) | 0.3 mg/l |
| Thiamine.HCl (sterile-filtered) | 0.2 mg/l |
| L-homoserine (sterile-filtered) | 0.4 g/l |
| $CaCO_3$ | 25 g/l |

The CSL (corn steep liquor), the MOPS (morpholinopropanesulfonic acid) and the salt solution are adjusted to pH 7 with aqueous ammonia and autoclaved. The sterile substrate and vitamin solutions and the dry-autoclaved $CaCO_3$ are then added.

Cultivation is carried out on a volume of 10 ml in a 100 ml conical flask with baffles at 33° C. and 80% atmospheric humidity.

After 48 hours the OD at a measurement wavelength of 660 nm is determined with a Biomek 1000 (Beckman Instruments GmbH, Munich). The amount of lysine formed is determined with an amino acid analyzer from Eppendorf-BioTronik (Hamburg, Germany) by means of ion exchange chromatography and post-column derivation with ninhydrin detection. Table 1 shows the result of the experiment.

TABLE 1

| Strain | OD (660 nm) | Lysine-HCl g/l |
|---|---|---|
| DM1637 | 13.2 | 7.21 |
| DM1637_lysC_S301F | 9.9 | 9.07 |

Obviously, numerous modifications and variations of the present invention are possible in light of the above teachings. It is therefore to be understood that within the scope of the appended claims, the invention may be practiced otherwise than as specifically described herein.

SEQUENCE LISTING

<160> NUMBER OF SEQ ID NOS: 11

<210> SEQ ID NO 1
<211> LENGTH: 1263
<212> TYPE: DNA
<213> ORGANISM: Corynebacterium glutamicum
<220> FEATURE:
<221> NAME/KEY: CDS
<222> LOCATION: (1)..(1263)
<223> OTHER INFORMATION: lysC wild-type gene

<400> SEQUENCE: 1

```
gtg gcc ctg gtc gta cag aaa tat ggc ggt tcc tcg ctt gag agt gcg      48
Val Ala Leu Val Val Gln Lys Tyr Gly Gly Ser Ser Leu Glu Ser Ala
1               5                   10                  15 gaa cgc att aga aac gtc gct gaa cgg atc gtt gcc acc aag aag gct      96
Glu Arg Ile Arg Asn Val Ala Glu Arg Ile Val Ala Thr Lys Lys Ala
            20                  25                  30 gga aat gat gtc gtg gtt gtc tgc tcc gca atg gga gac acg acg gat     144
Gly Asn Asp Val Val Val Val Cys Ser Ala Met Gly Asp Thr Thr Asp
        35                  40                  45 gaa ctt cta gaa ctt gca gcg gca gtg aat ccc gtt ccg cca gct cgt     192
```

```
Glu Leu Leu Glu Leu Ala Ala Ala Val Asn Pro Val Pro Pro Ala Arg
     50                  55                  60 gaa atg gat atg ctc ctg act gct ggt gag cgt att tct aac gct ctc        240
Glu Met Asp Met Leu Leu Thr Ala Gly Glu Arg Ile Ser Asn Ala Leu
 65                  70                  75                  80 gtc gcc atg gct att gag tcc ctt ggc gca gaa gcc caa tct ttc acg        288
Val Ala Met Ala Ile Glu Ser Leu Gly Ala Glu Ala Gln Ser Phe Thr
                 85                  90                  95 ggc tct cag gct ggt gtg ctc acc acc gag cgc cac gga aac gca cgc        336
Gly Ser Gln Ala Gly Val Leu Thr Thr Glu Arg His Gly Asn Ala Arg
            100                 105                 110 att gtt gat gtc act cca ggt cgt gtg cgt gaa gca ctc gat gag ggc        384
Ile Val Asp Val Thr Pro Gly Arg Val Arg Glu Ala Leu Asp Glu Gly
        115                 120                 125 aag atc tgc att gtt gct ggt ttc cag ggt gtt aat aaa gaa acc cgc        432
Lys Ile Cys Ile Val Ala Gly Phe Gln Gly Val Asn Lys Glu Thr Arg
130                 135                 140 gat gtc acc acg ttg ggt cgt ggt ggt tct gac acc act gca gtt gcg        480
Asp Val Thr Thr Leu Gly Arg Gly Gly Ser Asp Thr Thr Ala Val Ala
145                 150                 155                 160 ttg gca gct gct ttg aac gct gat gtg tgt gag att tac tcg gac gtt        528
Leu Ala Ala Ala Leu Asn Ala Asp Val Cys Glu Ile Tyr Ser Asp Val
                165                 170                 175 gac ggt gtg tat acc gct gac ccg cgc atc gtt cct aat gca cag aag        576
Asp Gly Val Tyr Thr Ala Asp Pro Arg Ile Val Pro Asn Ala Gln Lys
            180                 185                 190 ctg gaa aag ctc agc ttc gaa gaa atg ctg gaa ctt gct gct gtt ggc        624
Leu Glu Lys Leu Ser Phe Glu Glu Met Leu Glu Leu Ala Ala Val Gly
        195                 200                 205 tcc aag att ttg gtg ctg cgc agt gtt gaa tac gct cgt gca ttc aat        672
Ser Lys Ile Leu Val Leu Arg Ser Val Glu Tyr Ala Arg Ala Phe Asn
210                 215                 220 gtg cca ctt cgc gta cgc tcg tct tat agt aat gat ccc ggc act ttg        720
Val Pro Leu Arg Val Arg Ser Ser Tyr Ser Asn Asp Pro Gly Thr Leu
225                 230                 235                 240 att gcc ggc tct atg gag gat att cct gtg gaa gaa gca gtc ctt acc        768
Ile Ala Gly Ser Met Glu Asp Ile Pro Val Glu Glu Ala Val Leu Thr
                245                 250                 255 ggt gtc gca acc gac aag tcc gaa gcc aaa gta acc gtt ctg ggt att        816
Gly Val Ala Thr Asp Lys Ser Glu Ala Lys Val Thr Val Leu Gly Ile
            260                 265                 270 tcc gat aag cca ggc gag gct gcg aag gtt ttc cgt gcg ttg gct gat        864
Ser Asp Lys Pro Gly Glu Ala Ala Lys Val Phe Arg Ala Leu Ala Asp
        275                 280                 285 gca gaa atc aac att gac atg gtt ctg cag aac gtc tct tct gta gaa        912
Ala Glu Ile Asn Ile Asp Met Val Leu Gln Asn Val Ser Ser Val Glu
290                 295                 300 gac ggc acc acc gac atc acc ttc acc tgc cct cgt tcc gac ggc cgc        960
Asp Gly Thr Thr Asp Ile Thr Phe Thr Cys Pro Arg Ser Asp Gly Arg
305                 310                 315                 320 cgc gcg atg gag atc ttg aag aag ctt cag gtt cag ggc aac tgg acc       1008
Arg Ala Met Glu Ile Leu Lys Lys Leu Gln Val Gln Gly Asn Trp Thr
                325                 330                 335 aat gtg ctt tac gac gac cag gtc ggc aaa gtc tcc ctc gtg ggt gct       1056
Asn Val Leu Tyr Asp Asp Gln Val Gly Lys Val Ser Leu Val Gly Ala
            340                 345                 350 ggc atg aag tct cac cca ggt gtt acc gca gag ttc atg gaa gct ctg       1104
Gly Met Lys Ser His Pro Gly Val Thr Ala Glu Phe Met Glu Ala Leu
        355                 360                 365
```

```
cgc gat gtc aac gtg aac atc gaa ttg att tcc acc tct gag att cgt    1152
Arg Asp Val Asn Val Asn Ile Glu Leu Ile Ser Thr Ser Glu Ile Arg
    370                 375                 380 att tcc gtg ctg atc cgt gaa gat gat ctg gat gct gct gca cgt gca    1200
Ile Ser Val Leu Ile Arg Glu Asp Asp Leu Asp Ala Ala Ala Arg Ala
385                 390                 395                 400 ttg cat gag cag ttc cag ctg ggc ggc gaa gac gaa gcc gtc gtt tat    1248
Leu His Glu Gln Phe Gln Leu Gly Gly Glu Asp Glu Ala Val Val Tyr
                405                 410                 415 gca ggc acc gga cgc                                                1263
Ala Gly Thr Gly Arg
            420
```

<210> SEQ ID NO 2
<211> LENGTH: 421
<212> TYPE: PRT
<213> ORGANISM: Corynebacterium glutamicum

<400> SEQUENCE: 2

```
Val Ala Leu Val Val Gln Lys Tyr Gly Gly Ser Ser Leu Glu Ser Ala
1               5                   10                  15

Glu Arg Ile Arg Asn Val Ala Glu Arg Ile Val Ala Thr Lys Lys Ala
            20                  25                  30

Gly Asn Asp Val Val Val Cys Ser Ala Met Gly Asp Thr Thr Asp
        35                  40                  45

Glu Leu Leu Glu Leu Ala Ala Ala Val Asn Pro Val Pro Pro Ala Arg
    50                  55                  60

Glu Met Asp Met Leu Leu Thr Ala Gly Glu Arg Ile Ser Asn Ala Leu
65                  70                  75                  80

Val Ala Met Ala Ile Glu Ser Leu Gly Ala Glu Ala Gln Ser Phe Thr
                85                  90                  95

Gly Ser Gln Ala Gly Val Leu Thr Thr Glu Arg His Gly Asn Ala Arg
            100                 105                 110

Ile Val Asp Val Thr Pro Gly Arg Val Arg Glu Ala Leu Asp Glu Gly
        115                 120                 125

Lys Ile Cys Ile Val Ala Gly Phe Gln Gly Val Asn Lys Glu Thr Arg
    130                 135                 140

Asp Val Thr Thr Leu Gly Arg Gly Gly Ser Asp Thr Thr Ala Val Ala
145                 150                 155                 160

Leu Ala Ala Ala Leu Asn Ala Asp Val Cys Glu Ile Tyr Ser Asp Val
                165                 170                 175

Asp Gly Val Tyr Thr Ala Asp Pro Arg Ile Val Pro Asn Ala Gln Lys
            180                 185                 190

Leu Glu Lys Leu Ser Phe Glu Glu Met Leu Glu Leu Ala Ala Val Gly
        195                 200                 205

Ser Lys Ile Leu Val Leu Arg Ser Val Glu Tyr Ala Arg Ala Phe Asn
    210                 215                 220

Val Pro Leu Arg Val Arg Ser Ser Tyr Ser Asn Asp Pro Gly Thr Leu
225                 230                 235                 240

Ile Ala Gly Ser Met Glu Asp Ile Pro Val Glu Glu Ala Val Leu Thr
                245                 250                 255

Gly Val Ala Thr Asp Lys Ser Glu Ala Lys Val Thr Val Leu Gly Ile
            260                 265                 270

Ser Asp Lys Pro Gly Glu Ala Ala Lys Val Phe Arg Ala Leu Ala Asp
        275                 280                 285

Ala Glu Ile Asn Ile Asp Met Val Leu Gln Asn Val Ser Ser Val Glu
```

-continued

```
                    290                 295                 300
Asp Gly Thr Thr Asp Ile Thr Phe Thr Cys Pro Arg Ser Asp Gly Arg
305                 310                 315                 320

Arg Ala Met Glu Ile Leu Lys Lys Leu Gln Val Gln Gly Asn Trp Thr
                325                 330                 335

Asn Val Leu Tyr Asp Asp Gln Val Gly Lys Val Ser Leu Val Gly Ala
                340                 345                 350

Gly Met Lys Ser His Pro Gly Val Thr Ala Glu Phe Met Glu Ala Leu
            355                 360                 365

Arg Asp Val Asn Val Asn Ile Glu Leu Ile Ser Thr Ser Glu Ile Arg
            370                 375                 380

Ile Ser Val Leu Ile Arg Glu Asp Asp Leu Asp Ala Ala Ala Arg Ala
385                 390                 395                 400

Leu His Glu Gln Phe Gln Leu Gly Gly Glu Asp Glu Ala Val Val Tyr
                405                 410                 415

Ala Gly Thr Gly Arg
                420

<210> SEQ ID NO 3
<211> LENGTH: 1263
<212> TYPE: DNA
<213> ORGANISM: Corynebacterium glutamicum
<220> FEATURE:
<221> NAME/KEY: CDS
<222> LOCATION: (1)..(1263)
<223> OTHER INFORMATION: lysC allele lysC S301F

<400> SEQUENCE: 3 gtg gcc ctg gtc gta cag aaa tat ggc ggt tcc tcg ctt gag agt gcg      48
Val Ala Leu Val Val Gln Lys Tyr Gly Gly Ser Ser Leu Glu Ser Ala
1               5                   10                  15 gaa cgc att aga aac gtc gct gaa cgg atc gtt gcc acc aag aag gct      96
Glu Arg Ile Arg Asn Val Ala Glu Arg Ile Val Ala Thr Lys Lys Ala
                20                  25                  30 gga aat gat gtc gtg gtt gtc tgc tcc gca atg gga gac acc acg gat     144
Gly Asn Asp Val Val Val Val Cys Ser Ala Met Gly Asp Thr Thr Asp
            35                  40                  45 gaa ctt cta gaa ctt gca gcg gca gtg aat ccc gtt ccg cca gct cgt     192
Glu Leu Leu Glu Leu Ala Ala Ala Val Asn Pro Val Pro Pro Ala Arg
        50                  55                  60 gaa atg gat atg ctc ctg act gct ggt gag cgt att tct aac gct ctc     240
Glu Met Asp Met Leu Leu Thr Ala Gly Glu Arg Ile Ser Asn Ala Leu
65                  70                  75                  80 gtc gcc atg gct att gag tcc ctt ggc gca gaa gcc caa tct ttc acg     288
Val Ala Met Ala Ile Glu Ser Leu Gly Ala Glu Ala Gln Ser Phe Thr
                85                  90                  95 ggc tct cag gct ggt gtg ctc acc acc gag cgc cac gga aac gca cgc     336
Gly Ser Gln Ala Gly Val Leu Thr Thr Glu Arg His Gly Asn Ala Arg
            100                 105                 110 att gtt gat gtc act cca ggt cgt gtg cgt gaa gca ctc gat gag ggc     384
Ile Val Asp Val Thr Pro Gly Arg Val Arg Glu Ala Leu Asp Glu Gly
        115                 120                 125 aag atc tgc att gtt gct ggt ttc cag ggt gtt aat aaa gaa acc cgc     432
Lys Ile Cys Ile Val Ala Gly Phe Gln Gly Val Asn Lys Glu Thr Arg
    130                 135                 140 gat gtc acc acg ttg ggt cgt ggt ggt tct gac acc act gca gtt gcg     480
Asp Val Thr Thr Leu Gly Arg Gly Gly Ser Asp Thr Thr Ala Val Ala
145                 150                 155                 160 ttg gca gct gct ttg aac gct gat gtg tgt gag att tac tcg gac gtt     528
```

```
                                                                              -continued Leu Ala Ala Ala Leu Asn Ala Asp Val Cys Glu Ile Tyr Ser Asp Val
                165                 170                 175 gac ggt gtg tat acc gct gac ccg cgc atc gtt cct aat gca cag aag        576
Asp Gly Val Tyr Thr Ala Asp Pro Arg Ile Val Pro Asn Ala Gln Lys
            180                 185                 190 ctg gaa aag ctc agc ttc gaa gaa atg ctg gaa ctt gct gct gtt ggc        624
Leu Glu Lys Leu Ser Phe Glu Glu Met Leu Glu Leu Ala Ala Val Gly
        195                 200                 205 tcc aag att ttg gtg ctg cgc agt gtt gaa tac gct cgt gca ttc aat        672
Ser Lys Ile Leu Val Leu Arg Ser Val Glu Tyr Ala Arg Ala Phe Asn
    210                 215                 220 gtg cca ctt cgc gta cgc tcg tct tat agt aat gat ccc ggc act ttg        720
Val Pro Leu Arg Val Arg Ser Ser Tyr Ser Asn Asp Pro Gly Thr Leu
225                 230                 235                 240 att gcc ggc tct atg gag gat att cct gtg gaa gaa gca gtc ctt acc        768
Ile Ala Gly Ser Met Glu Asp Ile Pro Val Glu Glu Ala Val Leu Thr
                245                 250                 255 ggt gtc gca acc gac aag tcc gaa gcc aaa gta acc gtt ctg ggt att        816
Gly Val Ala Thr Asp Lys Ser Glu Ala Lys Val Thr Val Leu Gly Ile
            260                 265                 270 tcc gat aag cca ggc gag gct gcg aag gtt ttc cgt gcg ttg gct gat        864
Ser Asp Lys Pro Gly Glu Ala Ala Lys Val Phe Arg Ala Leu Ala Asp
        275                 280                 285 gca gaa atc aac att gac atg gtt ctg cag aac gtc ttt tct gta gaa        912
Ala Glu Ile Asn Ile Asp Met Val Leu Gln Asn Val Phe Ser Val Glu
    290                 295                 300 gac ggc acc acc gac atc acc ttc acc tgc cct cgt tcc gac ggc cgc        960
Asp Gly Thr Thr Asp Ile Thr Phe Thr Cys Pro Arg Ser Asp Gly Arg
305                 310                 315                 320 cgc gcg atg gag atc ttg aag aag ctt cag gtt cag ggc aac tgg acc       1008
Arg Ala Met Glu Ile Leu Lys Lys Leu Gln Val Gln Gly Asn Trp Thr
                325                 330                 335 aat gtg ctt tac gac gac cag gtc ggc aaa gtc tcc ctc gtg ggt gct       1056
Asn Val Leu Tyr Asp Asp Gln Val Gly Lys Val Ser Leu Val Gly Ala
            340                 345                 350 ggc atg aag tct cac cca ggt gtt acc gca gag ttc atg gaa gct ctg       1104
Gly Met Lys Ser His Pro Gly Val Thr Ala Glu Phe Met Glu Ala Leu
        355                 360                 365 cgc gat gtc aac gtg aac atc gaa ttg att tcc acc tct gag att cgt       1152
Arg Asp Val Asn Val Asn Ile Glu Leu Ile Ser Thr Ser Glu Ile Arg
    370                 375                 380 att tcc gtg ctg atc cgt gaa gat gat ctg gat gct gct gca cgt gca       1200
Ile Ser Val Leu Ile Arg Glu Asp Asp Leu Asp Ala Ala Ala Arg Ala
385                 390                 395                 400 ttg cat gag cag ttc cag ctg ggc ggc gaa gac gaa gcc gtc gtt tat       1248
Leu His Glu Gln Phe Gln Leu Gly Gly Glu Asp Glu Ala Val Val Tyr
                405                 410                 415 gca ggc acc gga cgc                                                   1263
Ala Gly Thr Gly Arg
            420

<210> SEQ ID NO 4
<211> LENGTH: 421
<212> TYPE: PRT
<213> ORGANISM: Corynebacterium glutamicum

<400> SEQUENCE: 4

Val Ala Leu Val Val Gln Lys Tyr Gly Gly Ser Ser Leu Glu Ser Ala
1               5                   10                  15

Glu Arg Ile Arg Asn Val Ala Glu Arg Ile Val Ala Thr Lys Lys Ala
```

-continued

```
            20                  25                  30
Gly Asn Asp Val Val Val Cys Ser Ala Met Gly Asp Thr Thr Asp
            35                  40                  45
Glu Leu Leu Glu Leu Ala Ala Val Asn Pro Val Pro Pro Ala Arg
 50                  55                  60
Glu Met Asp Met Leu Leu Thr Ala Gly Glu Arg Ile Ser Asn Ala Leu
 65                  70                  75                  80
Val Ala Met Ala Ile Glu Ser Leu Gly Ala Glu Ala Gln Ser Phe Thr
                 85                  90                  95
Gly Ser Gln Ala Gly Val Leu Thr Thr Glu Arg His Gly Asn Ala Arg
                100                 105                 110
Ile Val Asp Val Thr Pro Gly Arg Val Arg Glu Ala Leu Asp Glu Gly
            115                 120                 125
Lys Ile Cys Ile Val Ala Gly Phe Gln Gly Val Asn Lys Glu Thr Arg
 130                 135                 140
Asp Val Thr Thr Leu Gly Arg Gly Gly Ser Asp Thr Thr Ala Val Ala
 145                 150                 155                 160
Leu Ala Ala Ala Leu Asn Ala Asp Val Cys Glu Ile Tyr Ser Asp Val
                165                 170                 175
Asp Gly Val Tyr Thr Ala Asp Pro Arg Ile Val Pro Asn Ala Gln Lys
            180                 185                 190
Leu Glu Lys Leu Ser Phe Glu Glu Met Leu Glu Leu Ala Ala Val Gly
            195                 200                 205
Ser Lys Ile Leu Val Leu Arg Ser Val Glu Tyr Ala Arg Ala Phe Asn
 210                 215                 220
Val Pro Leu Arg Val Arg Ser Ser Tyr Ser Asn Asp Pro Gly Thr Leu
 225                 230                 235                 240
Ile Ala Gly Ser Met Glu Asp Ile Pro Val Glu Glu Ala Val Leu Thr
                245                 250                 255
Gly Val Ala Thr Asp Lys Ser Glu Ala Lys Val Thr Val Leu Gly Ile
            260                 265                 270
Ser Asp Lys Pro Gly Glu Ala Ala Lys Val Phe Arg Ala Leu Ala Asp
 275                 280                 285
Ala Glu Ile Asn Ile Asp Met Val Leu Gln Asn Val Phe Ser Val Glu
 290                 295                 300
Asp Gly Thr Thr Asp Ile Thr Phe Thr Cys Pro Arg Ser Asp Gly Arg
 305                 310                 315                 320
Arg Ala Met Glu Ile Leu Lys Lys Leu Gln Val Gln Gly Asn Trp Thr
            325                 330                 335
Asn Val Leu Tyr Asp Asp Gln Val Lys Val Ser Leu Val Gly Ala
                340                 345                 350
Gly Met Lys Ser His Pro Gly Val Thr Ala Glu Phe Met Glu Ala Leu
            355                 360                 365
Arg Asp Val Asn Val Asn Ile Glu Leu Ile Ser Thr Ser Glu Ile Arg
            370                 375                 380
Ile Ser Val Leu Ile Arg Glu Asp Asp Leu Asp Ala Ala Ala Arg Ala
 385                 390                 395                 400
Leu His Glu Gln Phe Gln Leu Gly Gly Glu Asp Glu Ala Val Val Tyr
                405                 410                 415
Ala Gly Thr Gly Arg
            420

<210> SEQ ID NO 5
```

```
<211> LENGTH: 1716
<212> TYPE: DNA
<213> ORGANISM: Corynebacterium glutamicum
<220> FEATURE:
<221> NAME/KEY: misc_feature
<222> LOCATION: (1)..(1716)
<223> OTHER INFORMATION: Description of the sequence: PCR product
      containing the upstream region of the lysC allele (= lysC S301F),
      and the CDS of the lysC allele and the downstream region

<400> SEQUENCE: 5
tacaattgtc cggtgtctga ccacggtgcc ccatgcgatt gttaatgccg atgctagggc      60
gaaaagcacg gcgagcagat tgctttgcac ttgattcagg gtagttgact aaagagttgc     120
tcgcgaagta gcacctgtca cttttgtctc aaatattaaa tcgaatatca atatatggtc     180
tgtttattgg aacgcgtccc agtggctgag acgcatccgc taaagcccca ggaaccctgt     240
gcagaaagaa aacactcctc tggctaggta gacacagttt ataaaggtag agttgagcgg     300
gtaactgtca gcacgtagat cgaaaggtgc acaaggtggg ccctggtcgt acagaaatat     360
ggcggttcct cgcttgagag tgcggaacgc attagaaacg tcgctgaacg gatcgttgcc     420
accaagaagg ctggaaatga tgtcgtggtt gtctgctccg caatgggaga caccacggat     480
gaacttctag aacttgcagc ggcagtgaat cccgttccgc cagctcgtga atggatatg     540
ctcctgactg ctggtgagcg tatttctaac gctctcgtcg ccatggctat tgagtccctt     600
ggcgcagaag cccaatcttt cacgggctct caggctggtg tgctcaccac cgagcgccac     660
ggaaacgcac gcattgttga tgtcactcca ggtcgtgtgc gtgaagcact cgatgagggc     720
aagatctgca ttgttgctgg tttccagggt gttaataaag aaacccgcga tgtcaccacg     780
ttgggtcgtg gtggttctga caccactgca gttgcgttgg cagctgcttt gaacgctgat     840
gtgtgtgaga tttactcgga cgttgacggt gtgtataccg ctgacccgcg catcgttcct     900
aatgcacaga agctggaaaa gctcagcttc gaagaaatgc tggaacttgc tgctgttggc     960
tccaagattt tggtgctgcg cagtgttgaa tacgctcgtg cattcaatgt gccacttcgc    1020
gtacgctcgt cttatagtaa tgatcccggc actttgattg ccggctctat ggaggatatt    1080
cctgtggaag aagcagtcct taccggtgtc gcaaccgaca agtccgaagc caaagtaacc    1140
gttctgggta tttccgataa gccaggcgag gctgcgaagg ttttccgtgc gttggctgat    1200
gcagaaatca acattgacat ggttctgcag aacgtctttt ctgtagaaga cggcaccacc    1260
gacatcacct tcacctgccc tcgttccgac ggccgccgcg cgatggagat cttgaagaag    1320
cttcaggttc agggcaactg gaccaatgtg ctttacgacg accaggtcgg caaagtctcc    1380
ctcgtgggtg ctggcatgaa gtctcaccca ggtgttaccg cagagttcat ggaagctctg    1440
cgcgatgtca acgtgaacat cgaattgatt tccacctctg agattcgtat ttccgtgctg    1500
atccgtgaag atgatctgga tgctgctgca cgtgcattgc atgagcagtt ccagctgggc    1560
ggcgaagacg aagccgtcgt ttatgcaggc accggacgct aaagttttaa aggagtagtt    1620
ttacaatgac caccatcgca gttgttggtg caaccggcca ggtcggccag gttatgcgca    1680
ccctttttgga agagcgcaat ttcccagcga attcgt                               1716

<210> SEQ ID NO 6
<211> LENGTH: 28
<212> TYPE: DNA
<213> ORGANISM: Artificial Sequence
<220> FEATURE:
<223> OTHER INFORMATION: Synthetic DNA
<220> FEATURE:
<221> NAME/KEY: misc_feature
```

```
<222> LOCATION: (1)..(28)
<223> OTHER INFORMATION: Primer lysCmfeA

<400> SEQUENCE: 6
tacaattgtc cggtgtctga ccacggtg                                    28

<210> SEQ ID NO 7
<211> LENGTH: 29
<212> TYPE: DNA
<213> ORGANISM: Artificial Sequence
<220> FEATURE:
<223> OTHER INFORMATION: Synthetic DNA
<220> FEATURE:
<221> NAME/KEY: misc_feature
<222> LOCATION: (1)..(29)
<223> OTHER INFORMATION: Primer lysCecoE

<400> SEQUENCE: 7
acgaattcgc tgggaaattg cgctcttcc                                   29

<210> SEQ ID NO 8
<211> LENGTH: 20
<212> TYPE: DNA
<213> ORGANISM: Corynebacterium glutamicum
<220> FEATURE:
<221> NAME/KEY: misc_feature
<222> LOCATION: (1)..(20)
<223> OTHER INFORMATION: Primer LC-lysC1-fbr

<400> SEQUENCE: 8
aaccgttctg ggtatttccg                                             20

<210> SEQ ID NO 9
<211> LENGTH: 20
<212> TYPE: DNA
<213> ORGANISM: Corynebacterium glutamicum
<220> FEATURE:
<221> NAME/KEY: misc_feature
<222> LOCATION: (1)..(20)
<223> OTHER INFORMATION: Primer LC-lysC2-fbr

<400> SEQUENCE: 9
tccatgaact ctgcggtaac                                             20

<210> SEQ ID NO 10
<211> LENGTH: 20
<212> TYPE: DNA
<213> ORGANISM: Corynebacterium glutamicum
<220> FEATURE:
<221> NAME/KEY: misc_feature
<222> LOCATION: (1)..(20)
<223> OTHER INFORMATION: Oligonucleotide lys301FC

<400> SEQUENCE: 10
tctacagaaa agacgttctg                                             20

<210> SEQ ID NO 11
<211> LENGTH: 35
<212> TYPE: DNA
<213> ORGANISM: Corynebacterium glutamicum
<220> FEATURE:
<221> NAME/KEY: misc_feature
<222> LOCATION: (1)..(20)
<223> OTHER INFORMATION: Oligonucleotide lys301FA

<400> SEQUENCE: 11
acgagggcag gtgaaggtga tgtcggtggt gccgt                            35
```

What is claimed is:

1. An isolated replicatable nucleic acid originating from *corynebacteria* and coding for an aspartokinase, wherein the amino acid sequence of the aspartokinase is SEQ ID NO: 2 in which the L-serine in position 301 is replaced by a different proteogenic amino acid.

2. The isolated replicatable nucleic acid of claim 1, wherein the amino acid in position 301 is L-phenylalanine.

3. The isolated replicatable nucleic acid of claim 1, wherein the amino acid in position 301 is selected from the group consisting of L-aspartic acid, L-asparagine, L-threonine, L-glutamic acid, L-glutamine, glycine, L-alanine, L-cysteine, L-valine, L-methionine, L-isoleucine, L-leucine, L-tyrosine, L-histidine, L-lysine, L-tryptophan, L-proline and L-arginine.

4. The isolated replicatable nucleic acid of claim 1, which is SEQ ID NO: 3.

5. The isolated replicatable nucleic acid of claim 1, which comprises the nucleotide sequence of SEQ ID NO: 1 in which the nucleotides at positions 901–903 are replaced with different nucleotides which encode a proteogenic amino acid other than L-serine.

6. The isolated replicatable nucleic acid of claim 5, wherein the nucleotide at position 902 is T.

7. The isolated replicatable nucleic acid of claim 1, which is a DNA.

8. A vector which contains the isolated replicatable nucleic acid of claim 1.

9. The vector of claim 7, which is a plasmid.

10. The vector of claim 8, which is replicable in *corynebacteria*.

11. A recombinant *corynebacteria* transformed with the vector of claim 8.

12. A recombinant *corynebacteria* which comprises the isolated replicatable nucleotide sequence of claim 1.

13. The *Corynebacteria* of claim 12, which overexpress the aspartokinase.

14. A process for producing L-lysine, comprising fermenting the *Corynebacteria* of claim 11 in a fermentation broth under conditions that the *Corynebacteria* produce L-lysine, and isolating the L-lysine.

15. A process for producing L-lysine, comprising fermenting in the *Corynebacteria* of claim 12 in a fermentation broth under conditions that the *Corynebacteria* produce L-lysine, and isolating the L-lysine.

16. A process for producing L-lysine, comprising fermenting in the *Corynebacteria* of claim 13 in a fermentation broth under conditions that the *Corynebacteria* produce L-lysine, and isolating the L-lysine.

17. The process of claim 16, wherein the amino acid in position 301 in the isolated replicatable nucleic acid is L-phenylalanine.

18. The method of claim 16, wherein the amino acid in position 301 in the isolated replicatable nucleic acid is selected from the group consisting of L-aspartic acid, L-asparagine, L-threonine, L-glutamic acid, L-glutamine, glycine, L-alanine, L-cysteine, L-valine, L-methionine, L-isoleucine, L-leucine, L-tyrosine, L-histidine, L-lysine, L-tryptophan, L-proline and L-arginine.

19. The method of claim 16, wherein the isolated replicatable nucleic acid comprises SEQ ID NO: 3.

20. The method of claim 16, wherein the isolated replicatable nucleic acid comprises the nucleotide sequence of SEQ ID NO: 1 in which the nucleotides at positions 901–903 are replaced with different nucleotides which encode a proteogenic amino acid other than L-serine.

21. The method of claim 20, wherein the nucleotide at position 902 is T.

* * * * *